(12) United States Patent
Costantino et al.

(10) Patent No.: US 6,719,970 B1
(45) Date of Patent: *Apr. 13, 2004

(54) METHOD OF GENERATING CARTILAGE

(75) Inventors: Henry R. Costantino, Grantham, NH (US); Lawrence J. Bonassar, Acton, MA (US); Mark A. Tracy, Arlington, MA (US)

(73) Assignees: Alkermes Controlled Therapeutics, Inc., Cambridge, MA (US); University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/612,744

(22) Filed: Jul. 10, 2000

(51) Int. Cl.[7] .............................. C12N 5/06; C12N 5/08; C12N 11/08
(52) U.S. Cl. ....................... 424/93.7; 435/180; 435/395
(58) Field of Search .................. 435/174, 177, 435/180, 395; 424/422, 423, 93.7

(56) References Cited

U.S. PATENT DOCUMENTS

| | | | |
|---|---|---|---|
| 3,523,906 A | 8/1970 | Vrancken et al. | 252/316 |
| 3,691,090 A | 9/1972 | Kitajima et al. | 252/316 |
| 3,737,337 A | 6/1973 | Schnoring et al. | 117/100 |
| 3,891,570 A | 6/1975 | Fukushima et al. | 252/316 |
| 3,960,757 A | 6/1976 | Morishita et al. | 252/316 |
| 4,389,330 A | 6/1983 | Tice et al. | 427/213.36 |
| 4,968,590 A | 11/1990 | Kuberasampath et al. | 530/326 |
| 5,011,691 A | 4/1991 | Oppermann et al. | 424/423 |
| 5,019,400 A | 5/1991 | Gombotz et al. | 424/497 |
| 5,041,138 A | 8/1991 | Vacanti et al. | 623/16 |
| 5,344,654 A | 9/1994 | Rueger et al. | 424/423 |
| 5,399,346 A | 3/1995 | Anderson et al. | 424/93.21 |
| 5,534,404 A | 7/1996 | Laurance et al. | 435/3 |
| 5,550,050 A | 8/1996 | Holland et al. | 435/240.2 |
| 5,654,010 A | 8/1997 | Johnson et al. | 424/502 |
| 5,656,297 A | 8/1997 | Bernstein et al. | 424/484 |
| 5,667,808 A | 9/1997 | Johnson et al. | 424/501 |
| 5,674,534 A | 10/1997 | Zale et al. | 424/501 |
| 5,711,968 A | 1/1998 | Tracy et al. | 424/487 |
| 5,716,644 A | 2/1998 | Zale et al. | 424/497 |
| 5,723,508 A | 3/1998 | Healy et al. | 521/61 |
| 5,786,216 A | 7/1998 | Dionne et al. | 435/402 |
| 5,795,790 A | 8/1998 | Schinstine et al. | 435/382 |
| 5,830,507 A | 11/1998 | Armstrong | 424/489 |
| 5,833,979 A | 11/1998 | Schinstine et al. | 424/93.21 |
| 5,842,477 A | 12/1998 | Naughton et al. | 128/898 |
| 5,853,385 A | 12/1998 | Emerich et al. | 604/49 |
| 5,902,741 A | 5/1999 | Purchio et al. | 435/240.23 |
| 5,916,585 A | 6/1999 | Cook et al. | 424/426 |
| 5,922,253 A | 7/1999 | Herbert et al. | 264/5 |
| 5,932,459 A | 8/1999 | Sittinger et al. | 435/180 |
| 5,944,754 A | 8/1999 | Vacanti | 623/11 |
| 5,955,438 A | 9/1999 | Pitaru et al. | 514/21 |
| 5,980,888 A | 11/1999 | Dimoudis et al. | 424/93.7 |
| 5,981,825 A | 11/1999 | Brekke | 623/11 |
| 6,017,708 A | 1/2000 | Piwnica-Worms | 435/6 |
| 6,027,721 A | 2/2000 | Hammang et al. | 424/93.2 |
| 6,045,818 A | 4/2000 | Cima et al. | 424/423 |
| 6,071,530 A | 6/2000 | Polson et al. | 424/426 |
| 6,071,708 A | 6/2000 | Jones et al. | 435/7.1 |
| 6,281,015 B1 | 8/2001 | Mooney et al. | 435/395 |

FOREIGN PATENT DOCUMENTS

| | | |
|---|---|---|
| WO | WO 96/18411 | 6/1996 |
| WO | WO 99/11789 | 3/1999 |

OTHER PUBLICATIONS

Babensee, J. E., et al., "Growth Factor Delivery for Tissue Engineering," *Pharmaceutical Research*, 17(5):497–504, May 2000.

*Primary Examiner*—David M. Naff
(74) *Attorney, Agent, or Firm*—Hamilton, Brook, Smith & Reynolds, P.C.

(57) ABSTRACT

The invention relates to an improved method for administering live cells to a patient and compositions useful in the method. The composition comprises live cells and biocompatible, biodegradable polymer microparticles. The cells and microparticles of the cell/microparticle composition can be contacted immediately prior to administration, or can be contacted in culture for a specified period of time prior to administration. In the method of the invention, an effective amount of the cell/microparticle composition is administered to a patient in need thereof by injection to a treatment site of the patient to provide a therapeutic effect in the patient. The therapeutic effect can be, for example, the formation of new tissue at the treatment site, or the production and secretion of a biologically active secretory molecule at the treatment site. The composition comprising lives cells and biocompatible, biodegradable polymer microparticles can further comprise a biologically active agent. In a preferred embodiment, the biologically active agent is incorporated into the microparticle. The biologically active agent can be, for example, factors which modulate cell growth.

12 Claims, 5 Drawing Sheets

Cells + μspheres 2 hrs 300X  3000X

Cells + μspheres 8 hrs

METHOD OF GENERATING CARTILAGE

BACKGROUND OF THE INVENTION

Implantable polymeric materials capable of being degraded and absorbed by the body have been used in medicine for many years. For example, implantable devices can be pre-seeded with a desired cell type, and used as structural supports or scaffolds for guiding tissue regeneration. One example is the regeneration of cartilage tissue using a degradable fiber mesh pre-seeded with chondrocytes as described in U.S. Pat. No. 5,041,138 to Vacanti et al. However, implantation of the scaffolds requires surgical intervention which presents disadvantages, such as the risk of infection and the need for invasive and painful procedures.

Suspensions of liquid hydrogel-cell compositions, which solidify in vivo following administration, have also been described as useful for the delivery of cells to a tissue surface in need of repair. See, for example, U.S. Pat. No. 5,944,754 to Vacanti. However, controlled delivery and containment of a liquid system within a particular area is difficult, and the liquid can spread to areas other than the implant site prior to solidification.

As such, a need exists for improved compositions and methods for administering live cells to a host to provide a therapeutic effect in the host, such as tissue regeneration.

SUMMARY OF THE INVENTION

The invention relates to an improved method for administering live cells to a patient and compositions useful in the method. The composition comprises live cells and biocompatible, biodegradable polymer microparticles. The cells and microparticles of the cell/microparticle composition can be contacted immediately prior to administration, or can be contacted in culture for a specified period of time prior to administration. In the method of the invention, an effective amount of the cell/microparticle composition is administered to a patient in need thereof by injection to a treatment site to provide a therapeutic effect in the patient. The therapeutic effect can be, for example, the formation of new tissue at the treatment site, or the production and secretion of a biologically active secretory molecule at the treatment site. The therapeutic effect resulting from injection of the cell/microparticle composition into a treatment site, is determined by the type of cell present in the composition.

Alternatively, the cell/microparticle composition of the invention can be used to generate in vitro tissue having a specific shape which can then be implanted in the patient at an implantation site to replace damaged tissue. The cell/microparticle composition is placed in a cell culture chamber having a desired shape. As the cells proliferate and adhere to the surfaces of the individual microparticles, a coherent mass of tissue having the shape of the culture chamber is formed. The formation of this coherent mass is referred to herein as "sintering". Sintering differs from other methods of preparing tissue in specific shapes, since it is the combination of cells and polymer microparticles which provide the matrix responsible for the shape of the resulting tissue rather than the polymer alone.

In a specific embodiment, the composition and method of the invention can be used for generating new tissue growth at a treatment site in a patient in need of tissue regeneration. The method for generating new tissue growth in a patient in need thereof comprises administering to the patient by injection into a treatment site an effective amount of a composition comprising biocompatible, biodegradable polymer microparticles and live cells capable of generating new tissue. The cells can be, for example, hepatocytes for the generation of liver tissue or chondrocytes for the generation of cartilage tissue. In a preferred embodiment, the cells are chondrocytes which generate cartilage tissue. In a more preferred embodiment, administration of the chondrocyte/microparticle composition is into the articular space of a joint of the patient.

As such, in a preferred embodiment, the invention relates to a method of generating new cartilage tissue in a patient in need thereof comprising administering by injection to a treatment site of the patient a composition comprising live chondrocytes and biocompatible, biodegradable polymer microparticles. The method and composition can be used for the treatment of cartilage deficiencies, defects, voids and conformational discontinuities in a patient.

In a further embodiment, the composition of the invention can be used in a method for secreting a biologically active secretory molecule in a patient in need of said molecule. The patient can be a mammal, such as a human. The method for secreting a biologically active secretory molecule in a patient in need of said molecule comprises administering to the patient by injection into a treatment site of the patient an effective amount of a composition comprising biocompatible, biodegradable polymer microparticles and live cells, wherein said cells are capable of secreting the biologically active secretory molecule.

In a particular embodiment, the cells are live pancreatic islet cells which secrete insulin. The composition comprising pancreatic islet cells and biocompatible, biodegradable polymer microparticles can be administered to the pancreas or other suitable treatment site of the patient. As such, the invention relates to a treatment for diabetes.

In another preferred embodiment, the cells are dopaminergic cells capable of secreting dopamine, such as PC-12 cells, adrenal chromaffin cells and fetal nigral primordia cells. The composition comprising live dopaminergic cells and biocompatible, biodegradable polymer microparticles can be administered to the striatum or other suitable treatment site of the patient in need thereof. Therefore, the invention relates to a treatment for Parkinson's disease.

In a particular embodiment, the composition comprising live cells and biocompatible, biodegradable polymer microparticles further comprises a biologically active agent. In a preferred embodiment, the biologically active agent is incorporated into the microparticle. The biologically active agent can be, for example, factors which modulate cell growth, such as factors having tissue regeneration inductive properties, for example, growth factors and differentiating factors, for example, morphogenic proteins; a cytokine; an extracellular matrix molecule; an antimicrobial agent; an anti-inflammatory agent; an immunosuppressive agent, cells which support the therapeutic effect of the administered cells or combinations thereof. Incorporation of the biologically active agent into the microparticles of the cell/microparticle composition provides a sustained delivery of the biologically active agent at the treatment site. It is preferred that the biologically active agent enhances the primary therapeutic effect resulting from administration of the live cell/microparticle composition.

The composition and methods of the present invention provide a means for eliciting a therapeutic effect in a patient in need thereof by administering a composition comprising lives cells and a biocompatible, biodegradable polymer microparticle. Advantageously, the composition permits the administration to be by injection which obviates the need for an open surgical intervention to permit exposure of the treatment area and the disadvantages associated with open surgery (e.g., pain, infection, recovery time and cost). In addition, the microparticles of the composition can have incorporated therein a biologically active agent thereby providing at the treatement site a sustained release of an agent which can be complementary to or enhance the primary treatment.

Advantages of the cell/microparticle composition are also realized when the composition is used to generate tissue in vitro having a specific shape. That is, sintering offers advantages over known methods of shaped tissue formation since a greater number of cells can be initially loaded into the culture chamber of a specified shape, thereby providing the needed tissue in a shorter period of time.

DETAILED DESCRIPTION OF THE INVENTION

Figure 1:
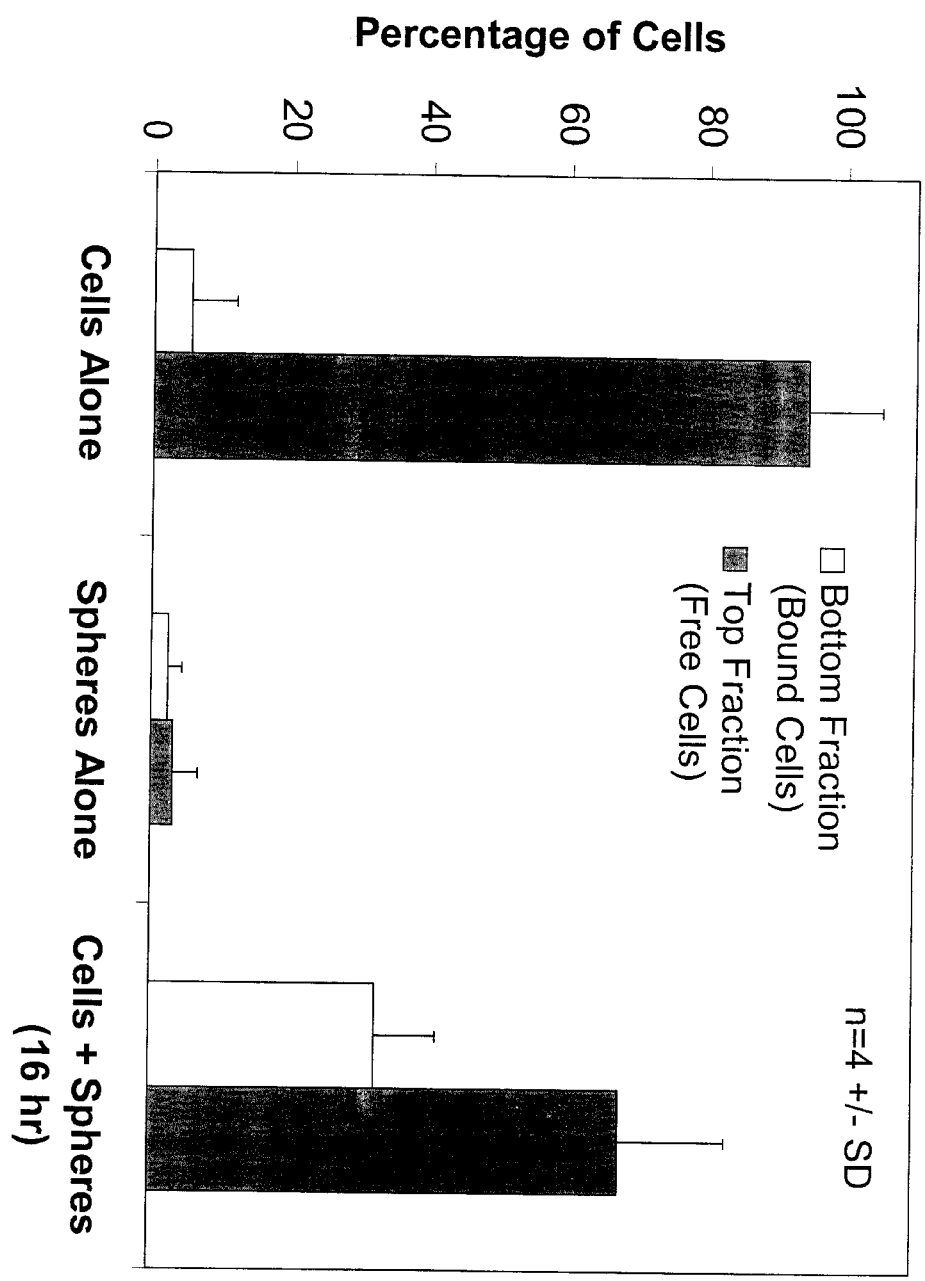
FIG. 1 is a graph showing the percentage of attached cells, in a cell/microparticle suspension, following a 16 hour incubation. The results of control mixtures of cells alone and microparticles alone are also shown.

The foregoing and other objects, features and advantages of the invention will now be more particularly described with reference to the accompanying drawings and pointed out in the claims. It is understood that the particular embodiments of the invention are shown by way of illustration and not as limitations of the invention. The principles of the invention can be employed in various embodiments without departing from the scope of the invention. A description of the preferred embodiments of the invention follows.

The present invention relates to a method of administering live cells to a patient in need thereof comprising injecting into a treatment site of the patient an effective amount of a composition comprising biocompatible, biodegradable polymer microparticles and live cells, wherein said cells provide a therapeutic effect in the patient.

The invention also relates to a composition comprising biocompatible, biodegradable polymer microparticles and live cells. It is understood that the live cells are responsible for the primary therapeutic effect and that the microparticles contribute to the retention of the cells at the treatment site and/or can provide a surface for cell growth. The microparticles and cells can be contacted immediately prior to administration, or can be contacted in culture for a desired period of time prior to administration. Preincubation can result in at least a portion of the cells to become attached to the microparticles prior to injection. However, as described herein, preincubation of the cells and microparticles is not needed in order to achieve a therapeutic effect following administration of the live cell/microparticle composition. When desired, the composition can further comprise a pharmaceutically acceptable carrier.

"Therapeutic effect", as that term is used herein, refers to the generation of new tissue at the treatment site, the secretion of a biologically active secretory molecule at the treatment site or a combination thereof.

Cells suitable for use in the invention include cells capable of generating tissue, cells which secrete biologically active secretory molecules, and cells which metabolize materials. Cell types that can be used for example, include but are not limited to, cartilage producing cells, for example, chondrocytes; fibroblasts; osteoblasts; exocrine cells; cells of intestinal origin; bile duct cells; parathyroid cells; thyroid cells; cells of the adrenal-hypothalamic-pituitary axis; organ cells, such as, heart cells, for example, heart muscle cells, kidney cells, for example, kidney epithelial cells, kidney tubular cells, and kidney basement membrane cells, liver cells, for example, hepatocytes, pancreatic cells, for example, pancreatic islet cells, lung cells, and brain cells; endothelial cells; mucosal cells; nerve cells; blood vessel cells; smooth muscle cells; skeletal muscle cells; pleural cells; Schwann cells; ear canal cells; tympanic membrane cells; peritoneal cells; tracheal epithelial cells macrophages; and dopaminergic cells capable of secreting dopamine, such as PC-12 cells, adrenal chromaffin cells and fetal nigral primordia cells, precursor cells of any of the above and stem cells.

Cells can be obtained directly from a donor, e.g., a patient's own cells, from a culture of cells from a donor of the same or a different species or from established cell culture lines. Preferably cells are of the same species and more preferably of the same immunological profile. Such cells can be obtained, for example, by biopsy either from the patient or a close relative. The cells are then grown in culture until confluent using standard cell culture techniques and conditions, and used when needed. Typically, cells are cultured only until a sufficient number of cells have been obtained for a particular application. For example, autologous cultured chondrocytes can be prepared according to the commercial process CARTICEL®

The cells can be genetically altered or manipulated using standard techniques prior to contacting them with the microparticles. For example, the cells can be genetically engineered to encode and secrete a desired biologically active secretory molecule and/or produce a desired tissue or enhance production of a desired tissue at a treatment site. For example, pancreatic islet cells can be genetically engineered to secrete enhanced amounts of insulin. Suitable method of genetically engineering cells can be found in U.S. Pat. No. 5,399,346 to Anderson et al., the entire content of which is incorporated herein by reference.

Cells can be cultured using any of the numerous well known cell culture techniques. Standard cell culture techniques are described in Freshney, "Cell Culture, A Manual of Basic Technique", Third Edition (Wiley-Liss, New York, 1994) the entire content of which is incorporated herein by reference.

In a particular embodiment, the composition comprising live cells and biocompatible, biodegradable polymer microparticles further comprises a biologically active agent. In a preferred embodiment, the biologically active agent can be incorporated into the microparticle. The biologically active agent can be, for example, factors which modulate cell growth, such as factors having tissue regeneration inductive properties, for example, a growth factor, a morphogenic protein, a cytokine, an immunosuppressive agent, an extracellular matrix molecule, an antimicrobial agent, an anti-inflammatory agent, cells which support the therapeutic effect of the administered cell or combinations thereof. Incorporation of the biologically active agent into the microparticles of the cell/microparticle composition provides a sustained delivery of the biologically active agent at the treatment site. It is preferred that the biologically active agent enhances the primary therapeutic effect resulting from administration of the cell microparticle composition.

"Treatment site" as that term is used herein refers to any internal structure or organ of the patient or a subcutaneous space needing treatment and includes, but is not limited to, joints including the articular space of the joints; internal organs, such as the liver, pancreas, brain, heart, lung and kidney; pleural cavities; the tracheal region; the thoracic cavity; the gastrointestinal tract; the genito-urinary tract; the bladder; vessels of the cardiovascular system; the gastointestinal tract including the stomach, colon and esophagus and subcutaeous spaces frequently accessed in cosmetic surgery, for example, the subcutaneous space involving the ear, cheek, nose etc.

For example, the therapeutic effect can be the generation of new tissue, often referred to as guided tissue regeneration. "Guided tissue regeneration" as that term is used herein refers to the restoration and/or regeneration of the morphology and function of hard and soft tissues that have been destroyed by disease or trauma. In tissue regeneration, the regenerating tissues repopulate the same site and space previously occupied by the healthy tissues that have been destroyed. As such, the composition and method of the invention can be used in a method for treating a tissue defect in a patient using guided tissue regeneration.

For example, the therapeutic effect can be the generation of new cartilage tissue. As such, the invention relates to a method of generating new cartilage tissue in a patient in need thereof comprising administering by injection to a treatment site of the patient a composition comprising live chondrocytes or other cartilage producing cells and biocompatible, biodegradable polymer microparticles. The method and composition can be used for the treatment of cartilage deficiencies, defects, voids and conformational discontinuities in the patient.

The need for cartilage regeneration can result from damage produced by diseases such as arthritis, trauma or congenital deformities. Damaged cartilage is a major cause of physical disability and deformity. For example, spinal discs, knees and hips are common sites of cartilage damage. The current therapy for loss of cartilage is replacement with a prosthetic material, such as silicon for cosmetic repairs or metal alloys for joint realignment. The use of a prosthesis is commonly associated with the significant loss of underlying tissue and bone without recovery of the full function allowed by the original cartilage. The prosthesis is also a foreign body which can become an irritating presence in the tissues. Other long-term problems associated with the permanent foreign body can include infection, erosion and instability. As such, the compositions and methods of the present invention provide a desirable alternative to current therapies for treating cartilage deficiencies.

"Cartilage" as used herein refers to a specialized type of dense connective tissue having cells embedded in a matrix. There are several kinds of cartilage. Hyaline cartilage is a bluish-white, glassy translucent cartilage having a homogeneous matrix containing collagenous fibers. Hyaline cartilage is found in articular cartilage, costal cartilage, the septum of the nose, the larynx and trachea. Articular cartilage is hyaline cartilage covering the articular surfaces of bones. Costal cartilage connects the ribs and the sternum. Fibrous cartilage contains collagen fibers. Yellow cartilage is a network of elastic fibers holding cartilage cells which is primarily found in the epiglottis, the external ear, and the auditory tube.

In another embodiment, the therapeutic effect can be the generation of new tissue of an internal organ. For example, the generation of tissues of the liver, brain, lung, pancreas, heart, and kidney. As such, the invention relates to a method of generating new internal organ tissue in a patient in need thereof comprising administering by injection to a treatment site of the patient a composition comprising live internal organ cells and biocompatible, biodegradable polymer microparticles. Preferably, the treatment site is the organ of the patient which is the same tissue type as the administered cells. More preferably the cells are of the same tissue type and species as the recipient organ. Most preferably, the cells are the patient's own cells of the same tissue type as the recipient organ. For example, the patient's hepatocytes can be preferably injected into the patient's liver.

In a further embodiment, the therapeutic effect can be the secretion of a biologically active secretory molecule in a patient in need of said molecule. As such, the invention relates to a method for secreting a biologically active secretory molecule in a patient in need of said molecule comprising administering to the patient by injection into a treatment site of the patient an effective amount of a composition comprising biocompatible, biodegradable polymer microparticles and live cells, wherein said cells secrete the biologically active secretory molecule.

In a particular embodiment, the cells are live pancreatic islet cells which secrete insulin. The composition comprising pancreatic islet cells and biocompatible, biodegradable polymer microparticles can be administered to the pancreas or other suitable treatment site of the patient. As such, the invention relates to a method for treating diabetes in a patient in need of treatment comprising administering to the patient by injection into a treatment site of the patient an effective amount of a composition comprising biocompatible, biodegradable polymer microparticles and live pancreatic islet cells, wherein said cells secrete insulin. In a preferred embodiment the treatment site is the pancreas. In another embodiment, the pancreatic islet cells can be genetically engineered to provide enhanced secretion of appropriate amounts of insulin in response to varying glucose levels as described in U.S. Pat. No. 5,534,404 to Laurance et al., the contents of which is incorporated herein by reference.

In another embodiment, the cells are dopaminergic cells capable of secreting dopamine, such as PC-12 cells, adrenal chromaffin cells and fetal nigral primordia cells. The composition comprising live dopaminergic cells and biocompatible, biodegradable polymer microparticles can be administered to the striatum or other suitable treatment site of the patient in need thereof. Therefore, the invention relates to a method for treating Parkinson's disease in a patient in need thereof, comprising administering to the patient by injection into a treatment site of the patient an effective amount of a composition comprising biocompatible, biodegradable polymer microparticles and live dopaminergic cells, wherein said cells secrete dopamine. In a preferred embodiment the treatment site is the striatum of the patient.

Other diseases such as hypoparathyroidism and anemia can be treated using cells in the cell/microparticle composition which secrete parathyroid hormone and erythropoietin, respectively. The secretory cells can be cells that naturally secrete the biologically active secretory molecule of interest or the cells can genetically engineered to do so or enhance the secretion of the desired biologically active secretory molecule. The cells can be chosen based on the biologically active secretory molecule desired. For example, the secretion of hormones, cytokines, growth factors, trophic factors, angiogenesis factors, antibodies, blood coagulation factors, lymphokines, enzymes and agonists, precursors, active analogs or active fragments thereof at a desired treatment site can be accomplished following the method of the invention described herein.

As such, the invention relates to a method of gene therapy comprising administering to the patient by injection into a treatment site of the patient an effective amount of a composition comprising biocompatible, biodegradable polymer microparticles and live cells which have been genetically engineered to secrete a biologically active secretory molecule. Such methods of gene therapy are described in, for example, U.S. Pat. No. 5,399,346 to Anderson et al.

In another embodiment, the invention relates to a method of restoring function to an organ or structure.

"Biologically active secretory molecule" as that term is used herein refers to a biologically active molecule which is released or secreted in vivo from a cell of the administered cell/microparticle composition. The biologically active secretory molecule can exert an effect on a separate target cell or on a target molecule in the patient. For example, hepatocytes can produce clotting factors and pancreatic islet cells can produce insulin and/or glycogen. The cells generally should retain normal morphology and cell function for the secretion of the bioactive molecules.

Examples of biologically active secretory molecules include, but are not limited to, hormones, cytokines, growth factors, trophic factors, angiogenesis factors, antibodies, blood coagulation factors, lymphokines, enzymes and agonists, precursors, active analogs or active fragments thereof at a desired treatment site can be accomplished following the method of the invention described herein.

An effective amount of the composition of this invention can be administered in vivo, for example, to a human, by injection at desired treatment site. As used herein, an "effective amount" is the amount needed to elicit the therapeutic effect, for example, new tissue formation and/or secretion of a biologically active secretory molecule in the patient following administration. For example, the composition can contain from about $0.5 \times 10^6$ cells/mL to about $50 \times 10^6$ cells/mL, such as from about $1 \times 10^6$ cells/mL to about $25 \times 10^6$ cells/mL. Further, the composition can contain microparticles at a concentration of about 1 mg/mL to about 500 mg/mL, such as from about 1 mg/mL to about 250 mg/mL, for example, 1 mg/mL to about 100 mg/mL.

"Injection" as that term is used herein, includes administration through a delivery port alone or in combination with a surgical scope such as a laparoscope, endoscope, laryngoscope, cystoscope, protoscope or thoracoscope. The delivery port can be, for example, a surgical tube such as a catheter with an appropriately sized bore, or a needle or needle-like port. As such, delivery can include a minor incision in the patient to permit entry of a delivery port, such as a needle or catheter, or a combination of a delivery port an a surgical scope. Advantageously, injection of the composition avoids the need for an open surgical procedure to expose the treatment area.

"Patient" as that term is used herein refers to the recipient of the treatment. Mammalian and non-mammalian patients are included. In a specific embodiment, the patient is a mammal, such as a human, canine, murine, feline, bovine, ovine, swine or caprine. In a preferred embodiment, the patient is a human.

In an alternative embodiment, the cell/microparticle composition can be used to prepare tissue having a specific shape. Currently, there is a lack of acceptably compatible, functional prosthesis to replace cartilage in individuals who have experienced loss of contoured cartilage, for example, noses or ear. Loss of contoured cartilage can result from burns or trauma. Typically, the patient is subjected to additional surgery involving carving a piece of cartilage out of a piece of lower rib to approximate the necessary contours and inserting the cartilage piece into a pocket of skin in the area where the nose or ear is missing. As such, the present invention provides a desirable treatment alternative for individuals needing repair of cartilage tissue wherein the tissue is in a specific anatomical shape.

Therefore, the invention relates to a method of generating new tissue having a specified anatomical shape comprising placing a composition comprising live cells and biocompatible, biodegradable polymer microparticles in a cell culture chamber having the specified anatomical shape and sintering the composition. Briefly, as the cells proliferate and adhere to the surfaces of the individual microparticles in culture, a coherent mass of tissue having the shape of the culture chamber is formed. The formation of this coherent mass is referred to herein as "sintering". Sintering differs from known methods of generating tissue in specific shapes, since it is the cells which are primarily responsible for the shape of the resulting tissue rather than the polymer matrix.

The term "biologically active agent," as used herein, is an agent, or its pharmaceutically acceptable salt, which when released in vivo, possesses the desired biological activity, for example therapeutic, diagnostic and/or prophylactic properties in vivo. It is understood that the term includes stabilized biologically active agents as described herein. A sustained release composition of the invention can contain from about 0.01% (w/w) to about 90% (w/w) of active agent (dry weight of composition). The amount of agent can vary depending upon the desired effect of the agent, the planned release levels, and the time span over which the agent is to be released. A preferred range of agent loading is between about 0.1% (w/w) to about 30% (w/w). A more preferred range of agent loading is between about 0.5% (w/w) to about 20% (w/w) agent.

When the composition comprising live cells and biocompatible, biodegradable polymer microparticles further comprises a biologically active, the biologically active agent can be, for example, factors which modulate cell growth, for example, factors having tissue regeneration inductive properties, such as growth factors, and differentiating factors, for example, morphogenic proteins, such as bone morphogenic proteins (BMPs) and osteogenic proteins (OPs). In a preferred embodiment, the biologically active agent is incorporated into the microparticle of the cell/microparticle composition.

Growth factors suitable for use include, but are not limited to, basic fibroblast growth factor (bFGF), platelet-derived growth factors (PDGF), transforming growth factors (TGF-α, TGF-β), cementum growth factors, epidermal growth factor (EGF), hepatocyte growth factor, heparin binding factor, insulin-like growth factors I or II (IGF-I, IGF-II), erythropoietin, and nerve growth factor (NGF).

Morphogenic proteins, which are capable of inducing bone and other tissue formation, include, but are not limited to, OP-1, OP-2, OP-3 (Osteogenic Protein), BMP2, BMP3, BMP4, BMP5, BMP6 and BMP7(Bone Morphogenic Protein). Morphogenic proteins and active fragments and derivatives of the proteins are described in, for example, U.S. Pat. No. 6,017,708 to Jones et al. issued on Jun. 6, 2000, U.S. Pat. No. 5,011,691 to Oppermann et al. issued on Apr. 30, 1991 and U.S. Pat. No. 4,968,590 to Kuberasampath et al. issued on Nov. 6, 1990 the entire contents of all of which are hereby incorporated by reference.

Other biologically active agents which can be present in the cell/microparticle composition, preferably incorporated into the microparticle of the cell/microparticle composition include antimicrobial agents, anti-inflammatory agents, immunosuppressive agents, extracellular matrix molecules, cytokines and cells which support the therapeutic effect of the administered cells.

Suitable antimicrobial agents include, but are not limited to, antibiotics such as penicillin and derivatives thereof, cephalosporins, tetracyclines, streptomycin, gentamicin and sulfonamide. Also included are antifungal agents such as myconazole.

Suitable immunosuppressive agents include, but are not limited to, cyclosporin, methotrexate or other agents whcih inhibit the immune response of the patient against the administered composition.

Examples of extracellular matrix molecules suitable for use in the cell/microparticle composition, preferably for incorporation into the microparticles of the cell/microparticle composition include, but are not limited to, fibronectin, laminin, collagens, and proteoglycans.

Cytokines suitable for use include, but are not limited to, lymphokines, chemokines and monokines. For example, the interleukins (IL), such as, IL-1 ($\alpha$ or $\beta$) IL-2, IL-3, IL-4, IL-5, IL-6, IL-7, IL-8, IL-9, IL-10, IL-11, IL-12, GM-CSF, M-CSF, LIF, LT, $\gamma$-IFN, $\alpha$-IFN, $\beta$-IFN, TNF-$\alpha$, BCGF, CD2, ICAM, MAdCAM, MCP-1, MCP-2, MCP-3.

The biologically active agent can be incorporated into the microparticles as is known in the art and described herein. It is understood that more that one agent can be incorporated into the microparticles of the composition. For example, agents can be coincorporated into the same microparticle or separately incorporated into separate microparticle and the microparticles mixed prior to administration. Alternatively, a biologically active agent can be administered without prior encapsulation to provide an immediate availability at the treatment site.

When the biologically active agent is a macromolecule, such as a protein, the agent can be a stabilized biologically active agent. The biologically active agent can be stabilized against degradation, loss of potency and/or loss of biological activity, all of which can occur during formation of the sustained release composition having the biologically active agent dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent or a specific combination of stabilizing agents. "Stabilizing agent", as that term is used herein, is any agent which binds or interacts in a covalent or non-covalent manner or is included with the biologically active agent. Stabilizing agents suitable for use in the invention are described in U.S. Pat. Nos. 5,716,644, 5,674,534, 5,654,010, 5,667,808, and 5,711,968, and co-pending U.S. patent application Ser. No. 08/934,830 to Burke et al., filed on Sep. 22, 1997, now U.S. Pat. No. 6,514,533, and Ser. No. 9/104,549 to Burke, filed on Jun. 25, 1998, now U.S. Pat. No. 6,265,389, the entire teachings of which are incorporated herein by reference.

For example, a metal cation can be complexed with the biologically active agent, or the biologically active agent can be complexed with a polycationic complexing agent such as protamine, albumin, spermidine and spermine, or associated with a "salting-out" salt. In addition, a specific combination of stabilizing agents and/or excipients may be needed to optimize stabilization of the biologically active agent.

Further, excipients can be added to maintain the potency of the biologically active agent over the duration of release and modify polymer degradation. Suitable excipients include, for example, carbohydrates, amino acids, fatty acids, surfactants, and bulking agents, and are known to those skilled in the art. An acidic or a basic excipient is also suitable. The amount of excipient used is based on ratio to the biologically active agent, on a weight basis. For amino acids, fatty acids and carbohydrates, such as sucrose, trehalose, lactose, mannitol, dextran and heparin, the ratio of carbohydrate to biologically active agent is typically between about 1:10 and about 20:1. For surfactants the ratio of surfactant to biologically active agent is typically between about 1:1000 and about 2:1. Bulking agents typically comprise inert materials. Suitable bulking agents are known to those skilled in the art.

The excipient can also be a metal cation component which acts to modulate the release of the biologically active agent. The metal cation component can optionally contain the same species of metal cation, as is contained in the metal cation stabilized biologically active agent, if present, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3.Mg(OH)_2.5H_2O$), $MgSO_4$, $Zn(OAc)_2$, $Mg(OAc)_2$, $ZnCO_3$ (such as $3Zn(OH)_2.2ZnCO_3$)$ZnSO_4$, $ZnCl_2$, $MgCl_2$, $CaCO_3$, $Zn_3(C_6H_5O_7)_2$ and $Mg_3(C_6H_5O_7)_2$.

A suitable ratio of metal cation component to polymer is between about 1:99 to about 1:2 by weight. The optimum ratio depends upon the polymer and the metal cation component utilized. A polymer matrix containing a dispersed metal cation component to modulate the release of a biologically active agent from the polymer matrix is further described in U.S. Pat. No. 5,656,297 to Bernstein et al. and co-pending U.S. patent application Ser. No. 09/056,566 filed on Apr. 7, 1998, now U.S. Pat. No. 5,912,051, the teachings of both of which are incorporated herein by reference in their entirety.

In yet another embodiment, at least one pore forming agent, such as a water soluble salt, sugar or amino acid, can be included in the sustained release composition to modify the microstructure. The proportion of pore forming agent in the microparticle can be from about 1% (w/w) to about 30% (w/w) of the final weight of the microparticle.

Incorporation of the biologically active agent into the microparticles of the cell/microparticle composition provides a sustained delivery of the biologically active agent at the treatment site. It is preferred that the biologically active agent enhances the primary therapeutic effect resulting from administration of the cell/microparticle composition. For example, the biologically active agent can promote tissue growth, inhibit infection at the treatment site or a combination thereof.

As used herein, the term "a" or "an" refers to one or more.

As used herein, the term "microparticles" refers to particles comprising biocompatible, biodegradable polymer having a volume median particle size of between about 1 and 1000 microns.

A "biocompatible polymer" as that term is used herein refers to polymer wherein any degradation products of the polymer are non-toxic to the recipient and also possess no significant deleterious or untoward effects on the recipient's body, such as a significant immunological reaction at the injection site.

"Biodegradable polymer", as defined herein, means the composition will degrade or erode in vivo to form smaller chemical species. Degradation can result, for example, by enzymatic, chemical and physical processes.

A biocompatible, biodegradable polymer therefor possesses the characteristics of both a biocompatible and biodegradable polymer. Suitable biocompatible, biodegradable polymers include, for example, poly(lactides), poly (glycolides), poly(lactide-co-glycolides), poly(lactic acid)s, poly(glycolic acid)s, polycarbonates, polyesteramides, polyanydrides, poly(amino acids), polyorthoesters, poly (dioxanone)s, poly(alkylene alkylate)s, copolymers of polyethylene glycol and polyorthoester, polyurethanes, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons. In a particular embodiment, the polymer is a poly(lactide-co-glycolide)(hereinafter "PLG") with a lactide:glycolide ratio of about 50:50 and a molecular weight of about 5,000 Daltons to about 70,000 Daltons.

A number of methods are known by which biocompatible, biodegradable polymer microparticles can be formed. In many cases the methods are described for embodiments wherein an active agent is incorporated into the polymer. However, it is to be understood that the methods described herein can be employed to prepare microparticles of biocompatible, biodegradable polymer which do not have an active agent incorporated therein. Suitable methods include, for example, spray-freeze drying, spray drying, single and double emulsion solvent evaporation, solvent extraction, phase separation, and simple and complex coacervation.

For example, methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biocompatible polymer, a polymer solvent and in some instances a biologically active agent is processed to create droplets, wherein at least a significant portion of the droplets contains polymer, polymer solvent and if applicable the active agent. These droplets are then frozen by a suitable means.

Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

A further example of a conventional process for producing microparticles is disclosed in U.S. Pat. No. 3,737,337, incorporated by reference herein, wherein a solution of a wall or shell forming polymeric material in a solvent is prepared. The solvent is only partially miscible in water. If desired a solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process to form microparticles which can contain a substance is disclosed in U.S. Pat. No. 3,523,906. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090 organic solvent is evaporated from a dispersion of microparticles in an aqueous medium, preferably under reduced pressure.

Similarly, the disclosure of U.S. Pat. No. 3,891,570 shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757.

Tice et al., in U.S. Pat. No. 4,389,330, describe the preparation of microparticles which can contain an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

When a biogically active agent is incorporated into the biocompatible, biodegradable polymer microparticles, it is believed that, without being bound by a particular theory, the release of the biologically active agent can occur by two different mechanisms. First, the biologically active agent can be released by diffusion through aqueous filled channels generated in the polymer matrix, such as by the dissolution of the biologically active agent, or by voids created by the removal of the polymer solvent during the preparation of the sustained release composition. A second mechanism is the release of the biologically active agent, due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer.

By altering the properties of the polymer, the contributions of diffusion and/or polymer degradation to biologically active agent release can be controlled. For example, increasing the glycolide content of a poly(lactide-co-glycolide) polymer and decreasing the molecular weight of the polymer can enhance the hydrolysis of the polymer and thus, provides an increased biologically active agent release from polymer erosion.

The live cell/biocompatible biodegradable polymer microparticle composition of the invention can optionally contain a pharmaceutically acceptable carrier. Pharmaceutically acceptable carriers are well known to those skilled in the art. The carrier should not deleteriously affect the cells, microparticles or, when present, the biologically active agent of the administered composition. It is preferred that the carrier includes factors which promote adhesion of the cells to the microparticles of the composition. For example, the medium in which the cells can be cultured can be suitable. Acceptable cell culture media are commercially available and are well known to those skilled in the art.

EXEMPLIFICATIONS

Preparative Methods

General Process for Preparing Microparticles

Formation of a mixture comprising a biocompatible polymer dissolved in a suitable polymer solvent and if desired a biologically active agent.

Optional homogenization of the mixture.

Atomization of the mixture to form droplets.

Freezing of the droplets by contact with liquid nitrogen.

Extraction of the polymer solvent from frozen droplets into an extraction solvent (e.g., −80° C. ethanol) thereby forming a solid polymer matrix.

Isolation of the solid polymer matrix particles from the extraction solvent by filtration.

Removal of remaining solvent by evaporation.

Sizing of particles by passage through an appropriately sized mesh.

EXAMPLE 1

Preparation of Microparticles

Microparticles were fabricated from PLG (50:50 lactide:glycolide, uncapped (—COOH), $M_w$~10 kDa) using the General Process outlined above.

EXAMPLE 2

Cell Isolation-Chondrocytes

Bovine articular cartilage was harvested from the gelnohumeral and humeroulnar joints of neonatal calves and digested in 0.3% Type II collagenase at 37° C. for 12–16 hours overnight with shaking. Chondrocytes were passed through a 180 μm filter to remove large particulate material. Cells were washed 3 times with PBS and resuspended in complete medium (Ham's F12, 10% FBS, 0.3% carboxymethylcellulose, pen/strep/amphotericin B, and ascorbic acid).

EXAMPLE 3

Chondrocyte/Microparticle Adhesion Assay

Chondrocytes were mixed with 3.57 mg/mL of PLG (50:50 L:G) microparticles, prepared as described above, to a final concentration of $1 \times 10^6$ cells/mL. Control groups included cells alone and microparticles alone at the same concentrations as described above. The mixture of cells and microparticles contained phosphate buffered saline and cell culture medium.

The combined cell/microparticle suspension and controls were incubated on a shaker plate at 37° C. At 0, 2, 4, 16 hours, 1 mL samples were removed and assayed to determine the amount of cells which had adhered to the microparticles. In order to determine the amount of cells which had adhered to the microparticles, each sample was loaded onto a 3 mL histopaque density gradient and centrifuged for 5 min at 5000 rpm. The unattached cells were removed by decanting the less dense media fraction on top of the histopaque (approximately 1 mL). The remaining portion (approximately 3 mL) contained the microparticles and attached chondrocytes. The results of the DNA assay provided data on the extent of attachment of the cells to the microparticles as well as the kinetics of the attachment of the cells to the microparticles. The DNA assay employed is described in Kim, Y. J. et al., "Analytical Biochemistry" Vol. 174, pp. 168–176 (1988).

Figure 2:
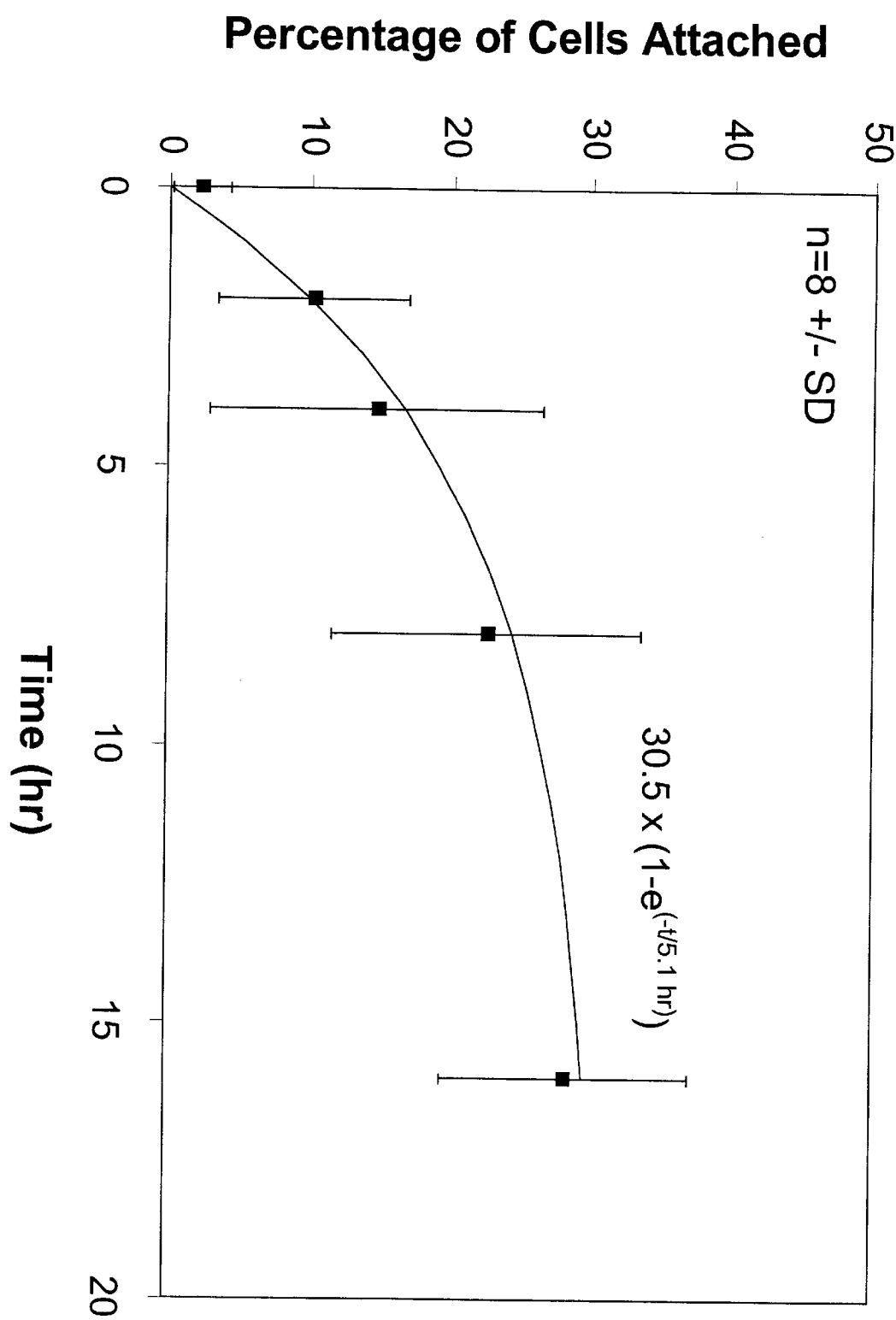
FIG. 2 is a graph showing the percentage of attached cells in a cell/microparticle suspension as a function of time.

The results from assaying for DNA content are shown graphically in FIGS. 1 and 2. The graphs in FIGS. 1 and 2 show that the cells exhibited first order binding and at about 16 hours 30% of the cells in the suspension were attached to the microparticles. In addition a value of about 5 hours for the exponential time constant, tau (τ), was determined from FIG. 2. Changes in cell morphology and matrix production were observed >16 hr.

EXAMPLE 4

Scanning Electron Microscopy

Figure 3:
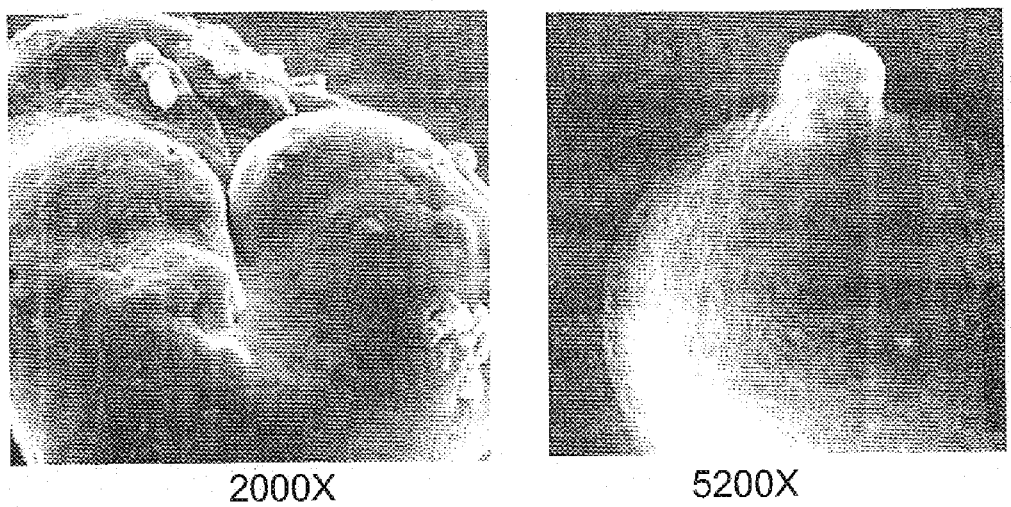
FIG. 3 is a Scanning Electron Micrograph (SEM), at the indicated magnifications, of a suspension of chondrocytes and microparticles following a 2 hour incubation.
Figure 4:
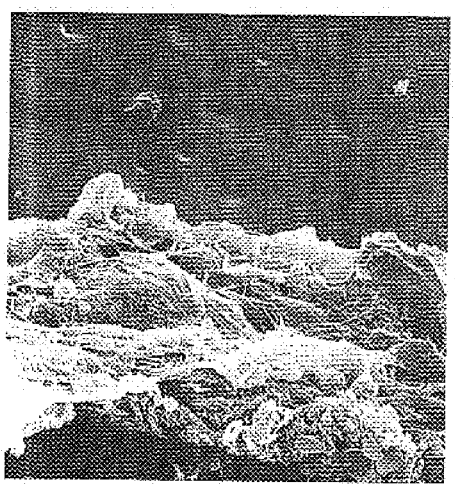
FIG. 4 is a Scanning Electron Micrograph (SEM), at the indicated magnifications, of a suspension of chondrocytes and microparticles following an 8 hour incubation.
Figure 4:

Scanning electron microscopy was conducted. Samples were removed from the cell/microparticle suspensions at 0, 2, 4, and 16 hours and analysed by SEM as described below. Glass coverslips were coated with a thin layer of TissueTack adhesive. Liquid samples (500 μL) of the cell/microparticle suspension were layered onto the coverslips in a 24 well plate and allowed to settle for 30 minutes. Samples were then fixed with 2.5% gluteraldehyde, critical point dried, sputter coated with Au/Pd and visualized via SEM. SEMs of the cell/microparticle suspension following 2 hours and 8 hours of incubation are shown in FIGS. 3 and 4 respectively, at the indicated magnifications. The SEMs showed attachment of cells to single microparticles at 2 hours, with large clusters of multiple cells and microparticles present at 16 hours.

In vivo Implantation and Analysis

Nude mice (5 per treatment group) were anesthetized with metofane and each received subcutaneous injections of 150 μL of a suspension of chondrocytes only, microparticles only, and chondrocytes and microparticles prepared as described above. The injections were at three individual sites on the dorsal aspect. The size of the implants were monitored superficially for 4 weeks, at which time, implants were harvested. Samples were weighed, photographed for gross morphology, and fixed in 10% buffered formalin for histology.

Fixed samples were embedded in paraffin and sectioned to 6 μm thick. Sections were then deparaffinized, rehydrated and stained in Mayer's hematoxylin and eosin (H&E).

Figure 5:
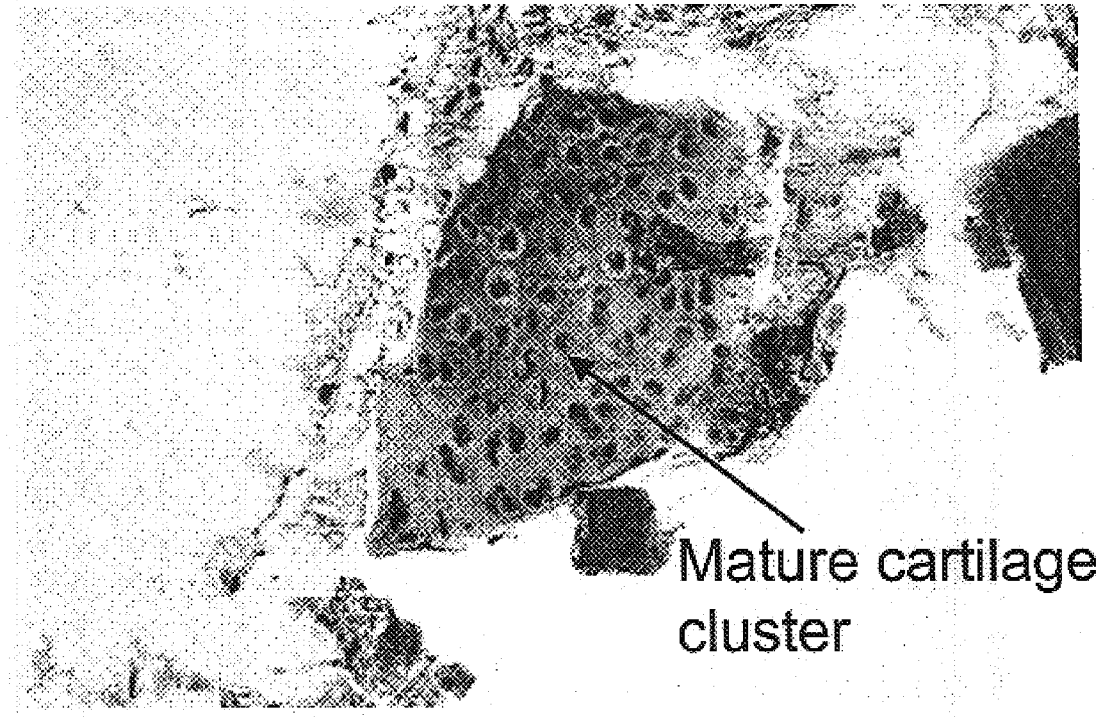
FIG. 5 is a section of tissue removed from the injection site of an animal receiving a mixture of PLG microparticles and chondrocytes following a 4 week treatment period. The section was stained with hematoxylin and eosin. The presence of a mature cartilage cluster is noted.

Gross analysis and H&E revealed formation of small nodules of tissue resembling cartilage for the group receiving a mixture of cells and microparticles. Animals receiving an injection of cells alone or microspheres alone did not yield any new cartilage growth. The results of H&E staining for animals receiving a mixture of cells and microparticles is shown in FIG. 5.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

What is claimed is:

1. A method of generating cartilage tissue in a patient in need thereof consisting essentially of administering by injection to a treatment site of the patient without open surgery to expose the treatment site an effective amount of a composition consisting essentially of live chondrocytes and biocompatible, biodegradable polymer microparticles wherein, the microparticles are injected in an amount sufficient to provide a surface for the chondrocytes to grow and generate said tissue.

2. The method of claim 1 wherein the the biocompatible, biodegradable polymer of the microparticle is selected from poly(lactides), poly(glycolides), poly(lactide-co-glycolides), poly(lactic acid)s, poly(glycolic acid)s, polycarbonates, polyesteramides, polyanydrides, poly (amino acids), polyorthoesters, poly(dioxanone)s, poly (alkylene alkylate)s, copolymers of polyethylene glycol and polyorthoester, polyurethanes, blends thereof, and copolymers thereof.

3. The method of claim 2 wherein the biocompatible, biodegradable polymer is a poly(lactide-co-glycolide).

4. The method of claim 1 wherein the composition further consisting essentially of a pharmaceutically acceptable carrier.

5. The method of claim 1 wherein the composition further consisting essentially of a biologically active agent.

6. The method of claim 5 wherein the biologically active agent has cartilage regeneration inductive properties.

7. The method of claim 5 wherein the biologically active agent is a growth factor or differentiating factor.

8. The method of claim 7 wherein the growth factor is selected from basic fibroblast growth factor (bFGF), platelet-derived growth factors (PDGF), transforming growth factors (TGF-α, TGF-β), cementum growth factors, epidermal growth factor (EGF), hepatocyte growth factor, heparin binding factor, insulin-like growth factors I or II (IGF-I, IGF-II), erythropoietin, and nerve growth factor (NGF).

9. The method of claim 7 wherein the differentiating factor is a morphogenic protein.

10. The method of claim 9 wherein the morphogenic protein is selected from OP-1, OP-2, OP-3, BMP2, BMP3, BMP4, BMP5, BMP6 and active fragments and derivatives thereof.

11. The method of claim 1 wherein the concentration of cells in the composition is from about $0.5 \times 10^6$ cells/mL to about $50 \times 10^6$ cells/mL.

12. The method of claim 1 wherein the treatment site is the articular space of a joint of the patient.

* * * * *